(12) United States Patent
Halas et al.

(10) Patent No.: US 6,778,316 B2
(45) Date of Patent: Aug. 17, 2004

(54) NANOPARTICLE-BASED ALL-OPTICAL SENSORS

(75) Inventors: Nancy J. Halas, Houston, TX (US); Surbhi Lal, Houston, TX (US); Peter Nordlander, Houston, TX (US); Joseph B. Jackson, Houston, TX (US); Cristin Erin Moran, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 10/280,481

(22) Filed: Oct. 24, 2002

(65) Prior Publication Data

US 2003/0174384 A1 Sep. 18, 2003

Related U.S. Application Data

(60) Provisional application No. 60/335,670, filed on Oct. 24, 2001, provisional application No. 60/339,415, filed on Oct. 26, 2001, and provisional application No. 60/369,079, filed on Apr. 1, 2002.

(51) Int. Cl.[7] .............................................. G02B 26/00
(52) U.S. Cl. ...................................... 359/296; 252/572
(58) Field of Search ......................... 359/296, 665–667; 204/450, 600; 252/572

(56) References Cited

U.S. PATENT DOCUMENTS

| 4,099,854 | A | * | 7/1978 | Decker et al. ............... 359/296 |
| 5,273,617 | A | | 12/1993 | Fathauer et al. ............. 117/105 |
| 5,365,054 | A | | 11/1994 | Fathauer et al. ............. 250/214 |
| 5,376,556 | A | | 12/1994 | Tarcha et al. ................ 436/525 |
| 5,479,024 | A | | 12/1995 | Hillner et al. ............ 250/458.1 |
| 5,567,628 | A | | 10/1996 | Tarcha et al. ................ 436/525 |
| 6,117,368 | A | * | 9/2000 | Hou ............................ 252/572 |
| 6,122,091 | A | | 9/2000 | Russell et al. ............... 359/245 |
| 6,331,276 | B1 | | 12/2001 | Takei et al. .............. 422/82.09 |
| 6,441,945 | B1 | | 8/2002 | Atwater et al. ............. 359/296 |
| 6,461,490 | B1 | | 10/2002 | Lennox et al. ......... 204/403.08 |
| 6,538,801 | B2 | * | 3/2003 | Jacobson et al. ........... 359/296 |
| 2002/0018610 | A1 | | 2/2002 | Challener et al. ............. 385/12 |

OTHER PUBLICATIONS

S.J. Oldenburg, et al; *Infrared Extinction Properties of Gold Nanoshells*; Applied Physics Letters, vol. 75, No. 19, Nov. 8, 1999; (pp. 2897–2899).

(List continued on next page.)

Primary Examiner—Georgia Epps
Assistant Examiner—M. Hasan
(74) Attorney, Agent, or Firm—Conley Rose, P.C.

(57) ABSTRACT

The present invention provides a sensor that includes an optical device as a support for a thin film formed by a matrix containing resonant nanoparticles. The nanoparticles may be optically coupled to the optical device by virtue of the geometry of placement of the thin film. Further, the nanoparticles are adapted to resonantly enhance the spectral signature of analytes located near the surfaces of the nanoparticles. Thus, via the nanoparticles, the optical device is addressable so as to detect a measurable property of a sample in contact with the sensor. The sensors include chemical sensors and thermal sensors. The optical devices include reflective devices and waveguide devices. Still further, the nanoparticles include solid metal particles and metal nanoshells. Yet further, the nanoparticles may be part of a nano-structure that further includes nanotubes.

11 Claims, 1 Drawing Sheet

OTHER PUBLICATIONS

S. R. Sershen, et al; *Independent Optically Addressable Nanoparticle–Polymer Optontechanical Composites*; Applied Physics Letters, vol. 80, No. 24, Jun. 17, 2002; (pp. 4609–4611).

H. R. Stuart, et al; *Island Size Efects in Nanoparticle–Enhanced Photodetectors*; Applied Physics Letters, vol. 73, No. 26, Dec. 28, 1998: (pp. 3815–3817).

H. R. Stuart, et al; *Enchanced Dipole–Dipole Interaction Between Elementary Radiators Near a Surface*; Physical Review Letters, vol. 80. No. 25. Jun. 22, 1998:(pp. 5663–5666).

S. Linden, et al; *controlling the Interaction Between Light and Gold Nanoparticles: Selective Suppression of Extinction*, Physical Review Letters, vol. 86, No. 20, May 14, 2001, (pp. 4688–4691).

J. B. Jackson, et al; *Controlling the Surfaced Enhanced Raman Effect with the Nanoshell Geometry*: Preprint (13 p.).

Cristin E. Moran, et al; *Mask–Free Passivative Stamp (MAPS) Lithography; Large Area Fabrication and Geometric Variation of Submicron Metal Line and Island Arrays*; Preprint (10 p.).

* cited by examiner

NANOPARTICLE-BASED ALL-OPTICAL SENSORS

CROSS-REFERENCE TO RELATED APPLICATIONS

This application claims the benefit of priority of U.S. Provisional Application 60/335,670, filed Oct. 24, 2001, entitled "Nanoshell-Based All-Optical Sensors", and U.S. Provisional Application 60/339,415, filed Oct. 26, 2001, entitled "Light Interaction Between Gold Nanoshells Plasmon Resonance and Planar Optical Waveguides". and U.S. Provisional Application 60/369,079, filed Apr. 1, 2002, entitled "Mask-Free Soft Lithographic Fabrication of Long-Range Planar 1D And 2D Metallic Arrays of Submicron Structures". Each of these applications is hereby incorporated herein by reference.

STATEMENT REGARDING FEDERALLY SPONSORED RESEARCH OR DEVELOPMENT

This invention was made with government support under Grant No. ECS-9801707 awarded by the National Science Foundation and Grant No. DAAD19-99-1-0315 awarded by the Army. The United States government has certain rights in the invention.

BACKGROUND OF THE INVENTION

1. Field of the Invention

The present invention relates generally to chemical sensors that detect changes in analyte concentration or changes in temperature. More particular, the present invention relates to such sensors that incorporate resonant nanoparticles embedded in a matrix that is supported by an optically addressable device.

2. Background of the Invention

Sensors are used to detect the concentration of an analyte and to detect the ambient temperature, among other applications. Chemical sensors based on surface plasmon resonance (SPR) are known. These sensors utilize the enhancement of Raman scattering from a Raman-active analyte that occurs when the analyte is brought near to a plasmon resonant surface. This enhancement is commonly termed surface enhanced Raman scattering (SERS).

The SERS effect is primarily related to the field strength near the surface of the substrate upon illumination, whether the substrate is a roughened metal surface or an aggregate of metallic nanoparticles. The strongest field enhancement is obtainable at the plasmon resonance of the metal substrate or particle. It is for this reason that gold colloid (plasmon resonance=520 nm) is such an efficient SERS enhancer under visible Raman excitation (typically with an argon ion laser at 514 nm).

Chemical sensors that incorporate metal nanoshells embedded in a matrix are described in commonly assigned co-pending patent application Ser. No. 09/616,154, now U.S. Pat No. 6,699,724 filed Jul. 14, 2000, hereby incorporated herein by reference. Metal nanoshells include composite, layered nanoparticles that may include a dielectric core and a metal shell.[1,2] Metal nanoshells are described in commonly assigned U.S. Pat. No. 6,344,272 and U.S. patent application Ser. No. 10/013,259, filed Nov. 5, 2001, each hereby incorporated herein by reference. By varying the relative dimensions of the core and shell layers, the optical absorption resonance of metal nanoshells can be controlled and tuned across a broad region of the optical spectrum from the visible to the mid infrared.[3] These frequency-agile properties are unique to nanoshells, and promise broad applicability across a range of technological applications.

Enormous increases in the detection sensitivity of molecules via the Surface-Enhanced Raman Effect can be achieved when the molecules of interest are on or near the surface of metal nanoshells and the metal nanoshell resonance is tuned to the wavelength of the excitation laser.[4] Enhancements of >$10^6$ with infrared excitation have been observed in highly absorptive solutions, which are equivalent to enhancements of $10^{12}$–$10^{14}$ in thin film geometries where the Raman signal is not reabsorbed. Furthermore, the metal nanoshell resonance can be tuned to the infrared region of the spectrum so that this detection capability can be realized in a region of the spectrum where compact and inexpensive semiconductor laser sources are available. This effect was recently exploited by one of the present inventors in the successful demonstration of an instantaneous immunoassay that can be performed in whole blood with no sample preparation.[5]

Nevertheless, despite continuing progress in SPR chemical sensors, there remains a need for a surface plasmon resonant chemical sensor having a controlled optical geometry.

SUMMARY OF THE INVENTION

The present invention is based on the discovery that an optical device may be used as a support for a thin film formed by resonant nanoparticles embedded in a matrix. The nanoparticles may be optically coupled to the optical device by virtue of the geometry of the thin film. Further, the nanoparticles are adapted to resonantly enhance the spectral signature of analytes located near the surfaces of the nanoparticles. Thus, via the nanoparticles, the optical device is addressable so as to detect a measurable property of a sample in contact with the sensor.

The optical device may be a reflective device. A reflective device preferably incorporates a reflective surface. For the purposes of the present specification a reflective surface denotes a surface having a ratio of reflectance to transmittance of at least 1.

Alternatively, the optical device may be a waveguide device. A thin film formed by the matrix and the embedded nanoparticles may serve as a cladding layer for the waveguide device.

The measurable property may be the concentration of the analyte in a sample in chemical contact with the matrix, where the chemical contact allows an exchange of analyte between the sample and the matrix.

Alternative, the measurable property may be the temperature of a sample or environment in thermal contact with the matrix, where the thermal contact allows an exchange of heat between the sample and the matrix.

The resonant nanoparticles are adapted to impart ultrahigh sensitivity to the sensor. Further, the sensor can be addressed and read out optically, providing remote sensing capabilities.

Thus, the present invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings, wherein like numbers refer to like elements.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

All-Optical Chemical Sensor

Referring initially to FIG. 1, according to an embodiment of the present invention, a chemical sensor 10 includes of a thin film 12 of resonant nanoparticles 14 embedded in a semipermeable matrix 16. Matrix 16 is preferably semipermeable, more preferably permeable to an analyte of interest.

Matrix 16 is preferably transparent to the optical sampling wavelength and not Raman active at the Stokes shifts of interest. The optical sample wavelength may be 820 nm. Alternatively, the optical sampling wavelength may be any suitable laser wavelength. Matrix 16 may be any suitable inorganic or polymeric material. One excellent candidate inorganic material for such a matrix material is mesoporous silica.

Figure 1A:
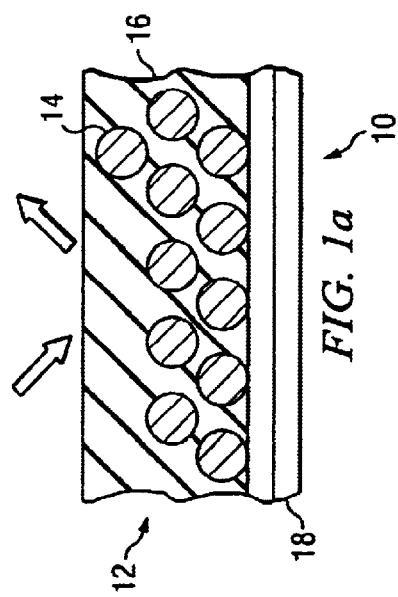
FIG. 1 is: (a) a cross-sectional view of a reflective chemical sensor according to an embodiment of the present invention; (b) a cross-sectional view of a waveguide chemical sensor according to another embodiment of the present invention.
Figure 1B:
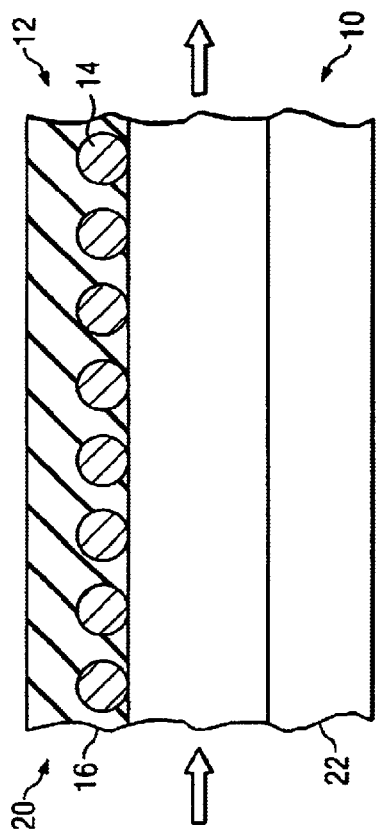

The basic device geometry is shown in FIG. 1. The optical sampling geometry can be as a layer deposited onto a reflective substrate 18 (FIG. 1(a)) exposed to incident light. Alternatively, the optical sampling geometry can be as a cladding layer 20 in a waveguide structure 22 (FIG. 1(b)), where the Raman excitation is a result of the evanescent wave of the guided optical mode propagating in that structure.

In either geometry, the analytes of interest are exposed to the semipermeable layer, diffuse through this layer and are adsorbed onto the surfaces of the embedded nanoparticles. The scattered light is modulated by the Stokes modes of the analyte molecules, and detection consists of spectral analysis of the scattered light using a standard dispersive geometry and lock-in based photodetection.

One direct advantage of Raman-based chemical sensing is its insensitivity to an $H_2O$ solvent. This approach can be used in analytical scenarios such as VOCs (volative organic compounds) in groundwater samples or hydrocarbon mixtures in petroleum refinery or recovery. This geometry should also be amenable to vapor phase sampling of analytes.

A further application is a biosensor, such as an immunoassay[11].

The analyte may be any suitable analyte such discloses in the present references[5,11] and/or in commonly assigned co-pending patent application Ser. No. 09/616,154, now U.S. Pat No. 6,699,724 filed Jul. 14, 2000. The analyte may be a Raman-active chemical to be detected. Alternatively, the analyte may be a complex of a non-Raman active chemical to be detected with a Raman-active moiety.

All-Optical Temperature Sensor

The active medium of this sensor consists of nanoparticles 30 whose resonances are tuned to match the pump laser wavelength.

The nanoparticles can be functionalized with molecules that exhibit a strong Raman response. A variety of candidate molecules may be used, such as para-mercaptoaniline, which can be bound to the surface of the nanoparticles and which yields three strong Stokes modes.

Alternatively the nanoparticles can be embedded in a medium 32 exhibiting a strong Raman response.

For high temperature operation, a composite of semiconducting carbon nanotubes 34 and nanoparticles 30 can be used. Since the peak amplitudes of the corresponding Stokes and anti-stokes modes of the Raman-active molecules are related by the Boltzmann distribution, their ratio provides an optical readout of the ambient temperature of the sensor.

Figure 2A:
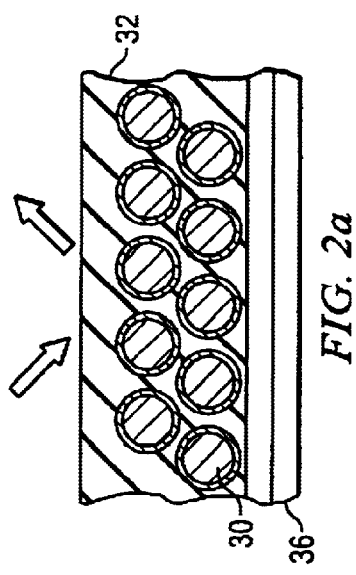
FIG. 2 is: (a) a cross-sectional view of a reflective thermal sensor according to an still another embodiment of the present invention; (b) a cross-sectional view of a waveguide thermal sensor according to yet another embodiment of the present invention.
Figure 2B:
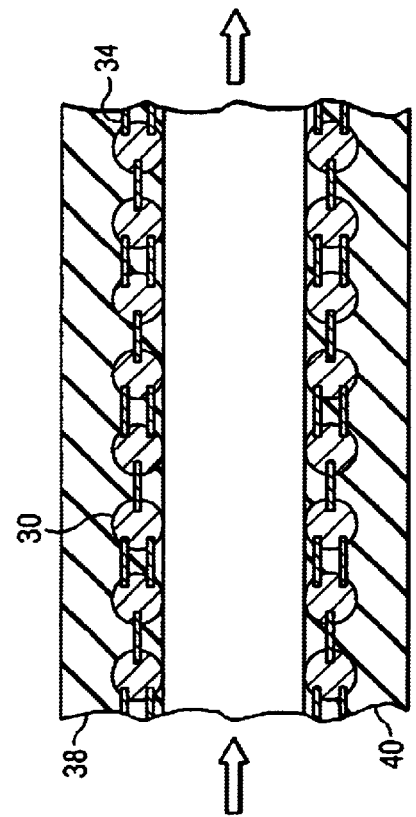

A schematic of this sensor is shown in FIG. 2. As for the chemical sensor described above, the optical sampling geometry can be as a layer deposited onto a reflective substrate 36 (FIG. 1(a)) exposed to incident light. Alternatively, the optical sampling geometry can be as a layer 38 in a waveguide structure 40 (FIG. 1(b)), where the Raman excitation is a result of the evanescent wave of the guided optical mode propagating in that structure.

This sensor can be designed for operation with a predetermined wavelength of light. According to some embodiments, the wavelength is 820 nm. Alternatively longer wavelengths, such as 1.06 µm may be selected, to eliminate the resonant Raman response when semiconducting carbon nanotubes are used.[6]

Nanoparticles

According to some embodiments, the resonant nanoparticles are solid metal nanoparticles. The shape of the metal nanoparticles may be selected so as to adjust the wavelength of the resonance. Thus, contemplated shapes include spheroids, ellipsoids, needles, and the like. Further the metal nanoparticles may be aggregated into multiparticle aggregates so as to adjust the wavelength of the resonance. Still further, the metal nanoparticles may be embedded in a matrix material that is capable of adjusting the wavelength of the resonance. For example, the matrix may be any dielectric material suitable to form the core of a metal nanoshell.

According to other embodiments, the resonant nanoparticles are metal nanoshells. The metal nanoshells may be metal nanoshells having multiple shell layers, termed herein multilayer nanoshells.

The wavelength of the resonance is preferably selected so as to provide surface enhanced Raman scattering. The wavelength may be controlled by controlling the geometry of the metal nanoparticle[12].

According to some embodiments of the present invention, the nanoparticles are islands, such as may be formed as a stamped surface[10].

According to some embodiments of the present invention, the nanoparticles are arranged in a random array. Random as used herein denotes lacking X-ray scattering peaks with the range of length scales up to mesoscopic. According to some embodiments of the present invention, the nanoparticles are arranged in a regular array. Regular as used herein denotes possessing at least one X-ray scattering peak with the range of length scales up to mesoscopic.

According to some embodiments of the present invention, the nanoparticles are arranged in a two dimensional array. Alternatively, according to some embodiments of the present invention, the nanoparticles are arranged in a three dimensional array. Yet alternatively, the thin film may contain an arrangement of nanoparticles having a fractional dimension between two and three.

Optical Device

It will be understood that the present optical device, such as a reflective device or a waveguide device, may be a component in an optical apparatus. Optical apparatuses that are contemplated include optical computing elements, holographic devices, optical correlators, optical phase conjugators, bistable memory devices, optical limiters, polarization filters, and infrared and visible light detectors.

When the optical device includes a reflective surface, the reflective surface may be a mirror. Alternatively, a reflective surface may a stack of dielectric thin films of alternating high and low refractive index. Such stacks are known that approach upwards of at least 90% reflectance. A spacer layer may be disposed between the reflective surface and the thin film containing the nanoparticles. The spacer layer may be formed of a dielectric material.

When the optical device includes a waveguide, the waveguide may include a dielectric layer supported on a metal layer. The thickness of the dielectric layer is preferably selected so as to support optical waves propagating parallel to the interface between the dielectric layer and the metal layer. The thin film layer containing the resonance nanoshells may form a cladding layer of the waveguide.

Methods of making the present optical devices include conventional microfabrication techniques such as known to one of ordinary skill in the art.

Optical Coupling

The thin film is preferably optically coupled to the optical device. The optical coupling preferably occurs as a result of the geometry of the thin film with respect to the optical device. It will be understood that the preferred average distance between a nanoparticle and a surface of the optical device may vary according to the wavelength of the maximum resonance of the nanoparticle, also termed herein resonant wavelength.

The average nanoparticle distance to the nearest surface of the optical device is preferably up to a value on the order of the resonant wavelength. The average distance to the nearest surface is preferably determined as the average length of a vector oriented perpendicular to the outer surface of the optical device and extending from that outer surface to the center of mass of a nanoparticle.

The average nanoparticle distance to a light directing surface as disclosed herein is likewise preferably up to a value on the order of the resonant wavelength. The average distance to the light directing surface is preferably determined as the average length of a vector oriented perpendicular to the light directing surface and extending from that light directing surface to the center of mass of a nanoparticle.

The light directing surface may be a metal surface in a waveguide. Alternatively, the light directing surface may be a reflective surface.

Exemplary light scattering experiments described in U.S. Provisional Application 60/339,415 that were performed on gold nanoshells randomly deposited on a dielectric layer supported on a gold layer show a change in the scattering spectrum of the nanoshells due to coupling of light with the waveguide modes. Thus, these experiments demonstrated optically coupling of metal nanoshells deposited on a waveguide structure with the waveguide. It is believed that these results extend to the present nanoparticles embedded in the present matrix supported on the present optical device.

Thin Film Formation

Forming the thin film preferably includes depositing a matrix material onto the optical device. The exposed surface of the optical device may be a metallic material. Alternatively, the exposed surface of the optical device may be a non-metallic material such as a dielectric material. The deposition may include spin-coating the matrix material. The matrix material may be in the form of a fluid precursor during the deposition. The formation of the thin film then includes drying the fluid precursor so as to form the matrix as a solid that is preferably still gas or liquid permeable. Suitable inorganic materials include silica or other oxides that may be formed by a sol-gel process. Suitable polymeric materials include polyvinyl acetate (PVA).

The nanoparticles may be mixed into the fluid precursor prior to deposition. Metal nanoshells have been successfully mixed by the present inventors into various polymers including PVA, polyvinylpropylene (PVP), polymethylmethacrylate (PMMA), and polydimethylsiloxane (PDMS). Further, methods for incorporating gold nanoparticles in a silica sol-gel matrix are known to one of ordinary skill in the art. These methods are contemplated for incorporating the present nanoparticles into inorganic oxide matrices.

Alternatively, nanoparticles or other nanostructure may be formed on the optical device so as to form a composite structure, followed by depositing the fluid precursor to the composite structure.

According to some embodiments, forming the composite structure includes evaporating a solution a concentrated solution of the nanoparticle. A suitable exemplary method in which the optical device is a waveguide and the nanoparticles are gold nanoshells is described in the paper entitled "Light Interaction Between Gold Nanoshell Plasmon Resonance and Planar Optical Waveguides" contained in Provisional Application No. 60/339,415, which is incorporated herein by reference.

In an exemplary method, an approximately 200 nm thick layer of gold was sputter coated onto an indium tin oxide (ITO) coated glass slide. Self-Assembled Monolayers (SAM's) of a cationic polyelectrolyte PDDA (poly (diallyldimethylammonium chloride) and anionic sheets of an exfoliated synthetic clay (Laponite RD, a synthetic form of hectorite) were deposited on the gold surface to control the spacing s to nominally nm precision between the gold surface and the gold nanoshells. A sub monolayer of gold nanoshells, with an average spacing of 200 nm and approximately 27% coverage (as determined by scanning electron microscopy) was deposited on the SAM's by evaporating 10–20 Ad of concentrated aqueous solution containing gold nanoshells.

According to other embodiments, forming the composite structure includes mask-free lithographic formation of metal structures, such as metallic arrays.

In an exemplary method[10], PDMS stamps were prepared in a standard way using an elastomer kit (Sylgard 184, Dow Corning). Diffraction gratings were purchased from Edmund Optics. Glass microscope slides were cleaned in piranha etch (7:3 v/v 98% $H_2SO_4$:30% $H_2O_2$) for 1 hour, rinsed in ultrapure water (Milli-Q system, Millipore) and dried with a stream of filtered $N_2$. n-Propyltrimethoxysilane (PTMS), $HAuCl_4$, and $K_2CO_3$ were purchased from Sigma-Aldrich Corp. and used as received. Silver plating was accomplished using a commercially available silver plating kit (HE-300, Peacock Laboratories Inc.) Scanning electron microscopy (SEM) was performed on a Phillips XL-30 ESEM. Atomic force microscopy (AFM) was performed on a Digital Instruments Nanoscope III.

Glass microscope slides were patterned with PTMS using stamps made from diffraction gratings and standard microcontact printing procedures. After the siloxane molecules had condensed on the surface (12 hours) the slides were exposed to a solution of $SnCl_2$ (Peacock Laboratories Inc.) for 5–10 seconds which activates the unstamped regions for metal reduction. Once activated the slides were washed with Milli-Q water and immediately exposed to silver or gold electroless plating solutions for a period of seconds or minutes until the metal had reduced onto the activated regions of the slides. Typical plating times ranged from 15 seconds to 1 minute. The silvering solution was used according to the provided instructions, while the gold solution was prepared by diluting 1 mL of a 1% $HAuCl_4$ solution in 100 mL $H_2O$ and adding 25 mg $K_2CO_3$. After plating samples were rinsed well with water and dried with filtered nitrogen.

References

The following references, referred to herein by accompanying number are hereby incorporated herein by reference in their entirety for all purposes:

1. R. D. Averitt, D. Sarkar & N. J. Halas. Plasmon Resonance Shifts of Au Coated Au2S Nanoshells: Insight into Multicomponent Nanoparticle Growth. *Physical Review Letters* 78, 4217–4220 (1997).
2. S. J. Oldenburg, R. D. Averitt, S. L. Westcott & N. J. Halas. Nanoengineering of Optical Resonances. *Chemical Physics Letters* 288, 243–247 (1998).
3. S. J. Oldenburg, J. B. Jackson, S. L. Westcott & N. J. Halas. Infrared Extinction Properties of Gold Nanoshells. *Applied Physics Letters* 75, 2897–2899 (1999).
4. S. J. Oldenburg, S. L. Westcott, R. D. Averitt & N. J. Halas. Surface Enhanced Raman Scattering in the near infrared using Metal Nanoshell Substrates. *Journal of Chemical Physics* 111, 4729–4735 (1999).
5. L. R. Hirsch, N. J. Halas & J. L. West. in *Biomedical Engineering Society Annual Meeting* (Seattle, Wash., 2000).
6. S. D. M. Brown, P. Corio, A. Marucci, M. S. Dresselhaus, M. A. Pimenta & K. Kneipp. Anti-Stokes Raman Specta of single-walled carbon nanotubes. *Physical Review B: Rapid Communications* 61, 5137–5140 (2000).
7. Y. Xia & G. M. Whitesides. Soft Lithography. *Angewandte Chemie International Edition* 37, 550–575 (1998).
8. K. F. Kelly, D. Sarkar, S. Prato, J. Resh, G. D. Hale & N. J. Halas. Direct Observation of fullerene-adsorbed tips by STM. *Journal of Vacuum Science and Technology B* 14, 593–596 (1996).
9. K. F. Kelly, G. D. Hale, D. Sarkar & N. J. Halas. Threefold Electron Scattering on Graphite Observed with C60-Modified STM Tips. *Science* 273, 1371–1373 (1996).
10. C. E. Moran, C. Radloff, and N. J. Halas. Mask-Free Passivation Stamp (MAPS) Lithography: Larger Area Fabrication and Geometric Variation of Submicron Metal Line and Island Arrays. Advanced Materials, v 15, n 10, 804–807 (2003). Preprint provided concurrently herewith.
11. L. R. Hirsch, J. B. Jackson, A. Lee, N. J. Halas, and J. L. West. A Rapid Whole Blood Immunoassay using Gold Nanoshells. Anal. Chem. 75, 2377 (2003). Preprint provided concurrently herewith.
12. J. B. Jackson, S. L. Westcott, L. R. Hirsch, J. L. West, and N. J. Halas, Controlling the Surface Enhanced Raman Effect with the Nanoshell Geometry. Appl. Phys. Lett., 82, 257 (2003). Preprint provided concurrently herewith.

Should the disclosure of any of the patents, patent applications, preprints, and publications that are incorporated herein conflict with the present specification to the extent that it might render a term unclear, the present specification shall take precedence.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. A sensor comprising:
   an optical device; and
   a thin film supported by said device, said thin film comprising
   a matrix; and
   a plurality of plasmon resonant particles embedded in said matrix;
   wherein said optical device is selected from the group consisting of a reflective device and a waveguide device.

2. A sensor comprising:
   an optical device; and
   a thin film supported by said device, said thin film comprising
   a matrix; and
   a plurality of plasmon resonant particles embedded in said matrix;
   wherein said sensor is selected from the group consisting of a chemical sensor and a thermal sensor.

3. A sensor comprising:
   an optical device;
   a thin film supported by said device, said thin film comprising
   a matrix; and
   a plurality of plasmon resonant particles embedded in said matrix; and
   a spacer layer disposed between said optical device and said thin film.

4. A sensor comprising:
   an optical device; and
   a thin film supported by said device, said thin film comprising
   a matrix;
   a plurality of plasmon resonant particles embedded in said matrix; and
   a plurality of carbon nanotubes embedded in said matrix.

5. A sensor comprising:
   an optical sampling member comprising a light directing surface;
   an optical enhancing member comprising:
   a matrix; and
   a plurality of resonant nanoparticles embedded in said matrix, and
   a spacer between said optical enhancing member and said optical sampling member;
   wherein said optical enhancing member is disposed so as to modify the optical response of the optical sampling member.

6. A sensor comprising:
   an optical sampling member comprising a light directing surface, said light directing surface comprising a reflective surface comprising the surface of a reflective dielectric thin film stack; and
   an optical enhancing member comprising:
   a matrix; and
   a plurality of resonant nanoparticles embedded in said matrix, wherein said optical enhancing member is disposed so as to modify the optical response of the optical sampling member.

7. A sensor comprising:

an optical sampling member comprising a light directing surface comprising a surface of a waveguide; and an optical enhancing member comprising:
  a matrix; and
  a plurality of resonant nanoparticles embedded in said matrix, wherein said optical enhancing member is disposed so as to modify the optical response of the optical sampling member.

8. The sensor of claim 7 wherein said light directive surface comprises the surface of a metal layer.

9. A sensor comprising:

an optical sampling member comprising a light directing surface; and an optical enhancing member comprising:
  a matrix; and
  a plurality of resonant nanoparticles embedded in said matrix, wherein said optical enhancing member is disposed so as to modify the optical response of the optical sampling member; and wherein said optical enhancing member enhances Raman scattering.

10. A sensor comprising:

an optical sampling member comprising a light directing surface; and an optical enhancing member comprising:
  a matrix; and
  a plurality of resonant nanoparticles embedded in said matrix, wherein said optical enhancing member is permeable to a preselected analyte and is disposed so as to modify the optical response of the optical sampling member.

11. A sensor comprising:

an optical sampling member comprising a light directing surface; and an optical enhancing member comprising:
  a matrix; and
  a plurality of resonant nanoparticles embedded in said matrix, said nanoparticles comprising Raman-active molecules absorbed thereon;

wherein said optical enhancing member is disposed so as to modify the optical response of the optical sampling member.

* * * * *